(12) United States Patent
Oda et al.

(10) Patent No.: US 8,569,012 B2
(45) Date of Patent: Oct. 29, 2013

(54) METHOD FOR STABILIZATION OF AQUEOUS ACRYLAMIDE SOLUTION

(75) Inventors: Masahito Oda, Kanagawa (JP); Katsuo Ishii, Kanagawa (JP)

(73) Assignee: Mitsubishi Rayon Co., Ltd., Tokyo (JP)

(*) Notice: Subject to any disclaimer, the term of this patent is extended or adjusted under 35 U.S.C. 154(b) by 0 days.

(21) Appl. No.: 12/922,340

(22) PCT Filed: Mar. 12, 2009

(86) PCT No.: PCT/JP2009/054775
§ 371 (c)(1),
(2), (4) Date: Sep. 13, 2010

(87) PCT Pub. No.: WO2009/113617
PCT Pub. Date: Sep. 17, 2009

(65) Prior Publication Data
US 2011/0006258 A1    Jan. 13, 2011

(30) Foreign Application Priority Data

Mar. 14, 2008 (JP) ................................. 2008-066094

(51) Int. Cl.
| C12P 1/00 | (2006.01) |
| C12N 9/88 | (2006.01) |
| C12N 1/21 | (2006.01) |
| C12P 13/02 | (2006.01) |

(52) U.S. Cl.
USPC .......... 435/41; 435/232; 435/129; 435/252.3; 435/252.31; 435/252.32; 435/252.33

(58) Field of Classification Search
USPC ..................... 435/232, 252.3, 252.31, 252.32, 435/252.33, 252.34, 129
See application file for complete search history.

(56) References Cited

U.S. PATENT DOCUMENTS

| 4,844,809 | A |   | 7/1989 | Ashina |         |
| 5,334,519 | A |   | 8/1994 | Yamada |         |
| 5,352,828 | A |   | 10/1994 | Seki |         |
| 5,698,629 | A |   | 12/1997 | Seki |         |
| 5,910,432 | A | * | 6/1999 | Ito et al. | 435/129 |
| 7,002,041 | B2 |   | 2/2006 | Abe |         |
| 7,129,217 | B2 | * | 10/2006 | Murao et al. | 514/23 |
| 7,205,133 | B2 |   | 4/2007 | Banba |         |
| 2003/0088125 | A1 |   | 5/2003 | Abe et al. |         |
| 2005/0064564 | A1 |   | 3/2005 | Petersen |         |
| 2007/0027294 | A1 | * | 2/2007 | Murao et al. | 528/310 |
| 2007/0184536 | A1 |   | 8/2007 | Greenhalgh |         |

FOREIGN PATENT DOCUMENTS

| EP | 0 515 123 A2 | 11/1992 |
| EP | 0515123 A2 | 11/1992 |
| EP | 1380 652 A1 | 1/2004 |
| JP | S39-10109 | 6/1964 |
| JP | S39-23548 | 10/1964 |
| JP | S40-07171 | 4/1965 |
| JP | S40-07172 | 4/1965 |
| JP | S41-01773 | 2/1966 |
| JP | S45-11284 | 4/1970 |
| JP | S47-04043 | 2/1972 |
| JP | S47-28766 | 7/1972 |
| JP | S48-03818 | 2/1973 |
| JP | S49-16845 | 4/1974 |
| JP | H05-49273 | 7/1993 |
| JP | H06-55148 | 7/1994 |
| JP | H07-265091 | 10/1995 |
| JP | 2548051 | 10/1996 |
| JP | H09-118704 | 5/1997 |
| JP | H09-275978 | 10/1997 |
| JP | 2002-281994 | 10/2002 |
| JP | 2003-206268 | 7/2003 |
| JP | 2003-221373 | 8/2003 |
| JP | 2003-221374 | 8/2003 |
| JP | 2004-528037 | 9/2004 |
| JP | 2007-512819 | 5/2007 |
| WO | WO 01/36592 | 5/2001 |
| WO | WO 03/033716 | 4/2003 |
| WO | WO 03/080680 | 10/2003 |
| WO | WO 2004/089518 | 10/2004 |
| WO | WO 2005/054488 | 6/2005 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Bratbak et al., Applied and Environmental Microbiology 48(4):755-757, 1984.*
International Search Report dated Apr. 28, 2009 for the instant U.S. National Phase application of International Application No. PCT/JP2009/054775.
A European Patent Office Examination Report, which issued on Jan. 30, 2012, during the prosecution of European Patent Application No. 09 719 738.8, which corresponds to this present application.

* cited by examiner

*Primary Examiner* — Delia Ramirez
(74) *Attorney, Agent, or Firm* — McDermott Will & Emery LLP

(57) ABSTRACT

The present invention provides a method for conveniently stabilizing an aqueous acrylamide solution using a stabilizer which can be separated and removed easily. In the method for stabilizing an aqueous acrylamide solution according to the present invention, a microbial cell is added to the aqueous acrylamide solution at a dried cell weight concentration of 1 to 14000 mg/L.

8 Claims, 1 Drawing Sheet

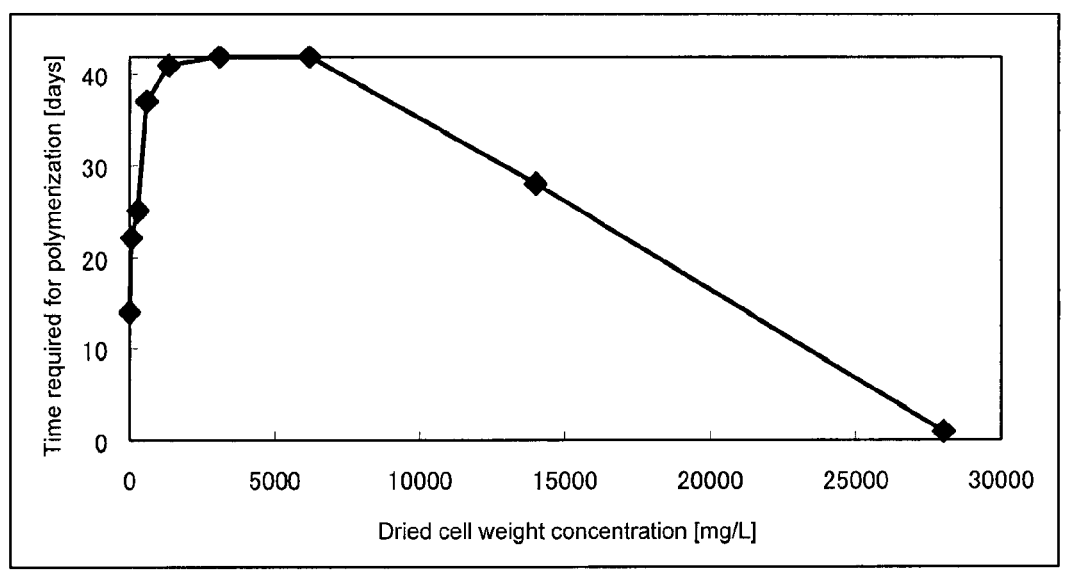

US 8,569,012 B2

METHOD FOR STABILIZATION OF AQUEOUS ACRYLAMIDE SOLUTION

CROSS REFERENCE TO PRIOR APPLICATIONS

This application is a U.S. National Phase application under 35 U.S.C. §371 of International Application No. PCT/JP2009/054775, filed on Mar. 12, 2009 and claims benefit of priority to Japanese Patent Application No. 2008-066094, filed on Mar. 14, 2008. The International Application was published in Japanese on Sep. 17, 2009 as WO 2009/113617 A1 under PCT Article 21(2). All of these applications are herein incorporated by reference.

TECHNICAL FIELD

The present invention relates to a method for stabilizing an aqueous acrylamide solution.

BACKGROUND ART

Acrylamide is widely utilized as a raw material for polymers used for many applications such as aggregating agents, thickening agents, oil recovery agents, paper power enhancing agents in the papermaking industry and thickening agents for papermaking. Examples of methods for industrially producing acrylamide include: a sulfuric acid hydrolysis method comprising the step of heating acrylonitrile with sulfuric acid and water to obtain amidosulfate; a method in which acrylonitrile is hydrated in the presence of a catalyst (e.g., metallic copper, copper oxide and copper salt); and a method in which acrylonitrile is hydrated using a microbial cell having nitrile hydratase activity.

Among such methods, a method using a microbial cell having nitrile hydratase activity is remarkably effective as a method for industrially producing acrylamide because reaction conditions are mild with almost no by-product and a very simple process can be employed. Further, using the method, a high-quality polyacrylamide having a significantly-high molecular weight with no insoluble impurity can be produced (Patent Document 1). For this reason, the method is the dominant method for producing acrylamide.

Like many other unsaturated monomers, acrylamide is easily polymerized by light and heat, and in addition, has a characteristic that it is significantly easily polymerized when brought into contact with the surface of iron. For this reason, in the production process of acrylamide, in order to stabilize acrylamide produced, the production is conducted under the conditions of light interception and low temperature (about 20° C.) and in the state in which contact with iron surface is avoided as much as possible. Further, addition of a stabilizer for suppressing polymerization of acrylamide is widely used.

Examples of stabilizers include 8-hydroxyquinoline, cupferron iron salt (Patent Document 2), thiourea, ammonium thiocyanate, nitrobenzol (Patent Document 3), ferron (Patent Document 4), furildioxime (Patent Document 5), a chromecyanogen complex (Patent Document 6), p-nitrosodiphenylhydroxylamine (Patent Document 7), 2,6-di-t-butyl-3-dimethylamino-4-methylphenol (Patent Document 8), 4-aminoantipyrine, oxalic acid, hydroxylamine sulfate (Patent Document 9), a mixture of manganese with a chelate compound (Patent Document 10), water-soluble monocarboxylic acid salt having at least two carbon atoms (Patent Document 11), a sulfur-containing compound and a mildly acidic salt (Patent Document 12).

As a method for preventing polymerization without using any stabilizer, a method for preventing polymerization of acrylamide which is prone to occur on the wall surface of the gas phase portion in an apparatus for use in the acrylamide production process by coating the wall surface of the gas phase portion with a synthetic resin-based material is shown (Patent Document 13).

Further, as a method for preventing polymerization of acrylamide which is prone to occur in a fluid accumulation portion in an apparatus for use in the acrylamide production process, the following methods are shown: a method in which a portion which may be in contact with a fluid accumulation portion is made of a resin (Patent Document 14); and a method for forcibly removing a process fluid accumulated in a fluid accumulation portion from the portion (Patent Document 15). Examples of such fluid accumulation portions include the inside of a pipe for sampling branched from the main pipe, a valve or the like. It is impossible to remove such a fluid accumulation portion by design choice. When a polymerized product is generated at a fluid accumulation portion, it may block the flow in a pipe, or the generated polymer may remove from the fluid accumulation portion and get mixed in with a process fluid, which may cause polymerization in a tank or the like downstream.

[Patent Document 1] Japanese Laid-Open Patent Publication No. H09-118704
[Patent Document 2] Japanese Publication for Opposition No. S39-23548
[Patent Document 3] Japanese Publication for Opposition No. S30-10109
[Patent Document 4] Japanese Publication for Opposition No. S40-7171
[Patent Document 5] Japanese Publication for Opposition No. S40-7172
[Patent Document 6] Japanese Publication for Opposition No. S41-1773
[Patent Document 7] Japanese Publication for Opposition No. S45-111284
[Patent Document 8] Japanese Publication for Opposition No. S47-4043
[Patent Document 9] Japanese Publication for Opposition No. S47-28766
[Patent Document 10] Japanese Publication for Opposition No. S48-3818
[Patent Document 11] Japanese Patent No. 2548051
[Patent Document 12] Japanese Laid-Open Patent Publication No. 2003-206268
[Patent Document 13] Japanese Publication for Opposition No. S49-16845
[Patent Document 14] Japanese Laid-Open Patent Publication No. 2003-221374
[Patent Document 15] Japanese Laid-Open Patent Publication No. 2003-221373

DISCLOSURE OF THE INVENTION

Problems to be Solved by the Invention

However, when using a method for adding a stabilizer like those described in Patent Documents 2-12, polymerization of acrylamide can be suppressed, but it is difficult to separate the stabilizer from the aqueous acrylamide solution after that. In a polymerized product obtained by polymerizing this acrylamide, the added stabilizer is contained as an impurity, and therefore, the quality of the polymerized product is reduced. Further, according to the methods of Patent Documents 13-15, production and operation of an apparatus for acrylamide production are complicated.

Under such circumstances, it has been desired to provide a convenient method for suppressing polymerization of an aqueous acrylamide solution using a stabilizer which is easily separated and removed during and after acrylamide production (that is, the method for stabilizing an aqueous solution of the present invention).

Means for Solving the Problems

The present invention was made in consideration of the above-described circumstances, and provides a method for stabilizing an aqueous acrylamide solution as described below.

A method for stabilizing an aqueous acrylamide solution, wherein a microbial cell is added to the aqueous acrylamide solution at a dried cell weight concentration of 1 to 14000 mg/L.

In the stabilization method of the present invention, the aforementioned dried cell weight concentration may be, for example, 10 to 14000 mg/L. Further, as the aforementioned microbial cell, for example, a microbial cell having nitrile hydratase activity can be used. In this regard, examples of the microbial cell having nitrile hydratase activity include microorganisms belonging to *Bacillus, Bacteridium, Micrococcus, Brevibacterium, Corynebacterium, Nocardia, Pseudomonas, Rhodococcus, Microbacterium* and *Rhodococcus rhodochrous*, and transformed microbial cells in which a nitrile hydratase gene is introduced. More specifically, examples thereof include *Rhodococcus rhodochrous* J-1 (Accession number: FERM BP-1478), *Rhodococcus rhodochrous* M8 (Accession number: VKPMB-S926) and *Escherichia coli* MT-10822 (Accession number: FERM BP-5785).

Advantageous Effect of the Invention

According to the method of the present invention, an aqueous acrylamide solution can be conveniently stabilized. In addition, it is also possible to easily separate and remove a stabilizer used.

BRIEF DESCRIPTION OF THE DRAWINGS

FIG. 1 shows the relationship between the dried cell weight concentration of the microbial cell contained in the aqueous acrylamide solution and time required for polymerization of acrylamide in the working examples of the present invention and comparative examples.

BEST MODES FOR CARRYING OUT THE INVENTION

Hereinafter, the method for stabilizing an aqueous acrylamide solution of the present invention will be described in detail. The scope of the present invention is not limited to the description. In addition to the following examples, the present invention can be suitably changed and then practiced within a range in which the effects of the present invention are not reduced.

Note that the entire specification of Japanese Patent Application No. 2008-066094 (filed on Mar. 14, 2008), to which priority is claimed by the present application, is incorporated herein. In addition, all the publications such as prior art documents, laid-open publications, patents and other patent documents cited herein are incorporated herein by reference.

In the method of the present invention, a microbial cell as a stabilizer is added to an aqueous acrylamide solution.

The aqueous acrylamide solution as used herein is an aqueous solution comprising 30 to 60% by mass, and preferably about 50% by mass of acrylamide. By adding a polymerization initiator such as ammonium persulfate to the aqueous acrylamide solution, acrylamide is polymerized to provide an aqueous polyacrylamide solution.

As the acrylamide of the present invention, a commercially-available acrylamide or the like can be used without limitation, but particularly preferred is an acrylamide produced from acrylonitrile using a microbial cell having nitrile hydratase activity (i.e., a microbial cell expressing nitrile hydratase enzyme).

As the microbial cell to be used as a stabilizer, various microbial cells can be used. Particularly preferred is a microbial cell having nitrile hydratase activity. This is because, when producing an acrylamide using the microbial cell having nitrile hydratase activity, there is no need to separately add the microbial cell as a stabilizer, and therefore the process can be simplified.

The microbial cell having nitrile hydratase activity means a microbial cell obtained by culturing a microorganism expressing nitrile hydratase enzyme or a product obtained by treating the microbial cell. The microbial cell or the product obtained by treating the microbial cell is a cell per se subjected to washing or chemical treatment according to need or a fractured product of the cell, or a product in which the cell or fractured product of the cell is immobilized using the entrapping immobilization method, cross-linking method, carrier binding method or the like. In the present invention, a microbial cell not subjected to entrapping immobilization is particularly preferred.

Examples of the method for washing the microbial cell include a method of using an aqueous acrylic acid solution (Japanese Laid-Open Patent Publication No. 2002-281994). Examples of the chemical treatment for the microbial cell include a cross-linking treatment using glutaraldehyde (Japanese Laid-Open Patent Publication No. H07-265091) and a sterilization treatment using a surfactant (International Publication WO 01/036592 pamphlet).

The form in which entrapping immobilization is not performed is a form in which the cell membrane of a microorganism is in direct contact with a reaction solution. For example, it means a form in which a cell is not enclosed with a polymer substance such as polyacrylamide, polyvinyl alcohol, carrageenan, agar, gelatin and alginic acid using the entrapping immobilization method.

Examples of the microbial cell having nitrile hydratase activity include microbial cells belonging to *Bacillus, Bacteridium, Micrococcus, Brevibacterium, Corynebacterium, Nocardia, Pseudomonas, Rhodococcus, Microbacterium* and *Rhodococcus rhodochrous*. In addition, transformed microbial cells, in which a naturally-occurring or artificially-improved nitrile hydratase gene is introduced (artificially incorporated) into a microbial cell to enable nitrile hydratase enzyme to be constitutively expressed, may also be used. More specifically, for example, *Rhodococcus rhodochrous* J-1 (Accession number: FERM BP-1478), *Rhodococcus rhodochrous* M8 (Accession number: VKPMB-S926) and *Escherichia coli* MT-10822 (Accession number: FERM BP-5785) are preferably used. The above-described transformed microbial cells can be prepared using publicly-known gene sequence information, genetic engineering techniques, etc. The above-described FERM strains can be obtained from International Patent Organism Depositary, National Institute of Advanced Industrial Science and Technology. The above-described VKPMB can be obtained from Russian National Collection of Industrial Microorganisms (VKPM) 1-st Dorozhny Proezd, b.1, Moscow, Russia.

Examples of microbial cells other than the microbial cell having nitrile hydratase activity include *Escherichia coli* and *Bacillus subtills* IF03335.

These microbial cells may be used solely or in combination.

In the method of the present invention, the aforementioned microbial cell is contained in an aqueous acrylamide solution so that the dried cell weight concentration becomes preferably 1 to 14000 mg/L, more preferably 10 to 14000 mg/L, even more preferably 10 to 6500 mg/L, still more preferably 10 to 500 mg/L, particularly preferably 10 to 300 mg/L, and most preferably 10 to 200 mg/L. When the content of the microbial cell contained in the aqueous solution is within the above-described range of the dried cell weight concentration, the effect of preventing polymerization of acrylamide can be sufficiently obtained. As used herein, "dried cell weight concentration" (mg/L) means a content ratio (concentration) of the dry weight (mg) of a desired microbial cell contained in an aqueous acrylamide solution relative to the volume (L) of the entire aqueous solution.

By setting the content of the microbial cell in the aqueous acrylamide solution (dried cell weight concentration) to a lower amount within the aforementioned range, foamability of the aqueous acrylamide solution is reduced. Therefore, it becomes easy to handle the aqueous acrylamide solution even in the case where there are subsequent processes such as concentration, distillation, crystallization and polymerization. Further, when the aqueous acrylamide solution is shipped out as it is as a product, the product is less likely to foam, and transportation and transfusion become easy. Foamability of an aqueous acrylamide solution obtained becomes lower when the aforementioned content (dried cell weight concentration) is 500 mg/L or lower, and further lower when the content is 300 mg/L or lower. Therefore, there is no need to consider the problem of foaming.

The method for adding the microbial cell to the aqueous acrylamide solution is not particularly limited as long as the microbial cell can be added in a desired content. The microbial cell may be added to the prepared aqueous acrylamide solution later so that a desired content can be provided. Alternatively, as long as no trouble is caused at the time of preparation of aqueous acrylamide solution, the aqueous acrylamide solution may be prepared in a state where the microbial cell has been added.

When the microbial cell to be used as a stabilizer is a microbial cell having nitrile hydratase activity, the aforementioned microbial cell used as a catalyst for producing acrylamide from acrylonitrile is retained as it is or concentrated, thereby providing a desired content.

The dried cell weight concentration of the microbial cell to be contained in the aqueous acrylamide solution in the present invention can be measured according to the method described below.

(1) An aqueous acrylamide solution comprising a microbial cell (volume V) is added to a centrifuge tube having an inner volume of 50 mL (tare weight has been measured) to perform centrifugation (15° C., 15000 G, 5 minutes).
(2) Subsequently, supernatant is removed and then the same amount of water is added to the centrifuge tube. After the pellet is resuspended, centrifugation is performed (15° C., 15000 G, 5 minutes).
(3) Item (2) above is repeated several times.
(4) After supernatant is removed, the weight ($W_1$) of the obtained pellet is measured.
(5) A portion of the obtained pellet is added to an aluminium plate, whose tare weight has been measured, to measure the additive amount ($W_2$).
(6) The aforementioned aluminium plate is covered with an aluminium foil, and after that, it is left in a drying machine (constant temperature: 120° C.) for 3 hours. Then the dried cell weight ($W_3$) is measured.

Using the values $W_1$ to $W_3$, the dried cell weight concentration ($C_4$) of the microbial cell contained in the aqueous acrylamide solution is calculated according to formula (I) below:

$$C_4 [mg/L] = W_3 [g]/W_2 [g] * W_1 [g]/V [mL] \times 10^6 \qquad (I)$$

Further, the dried cell weight concentration of the microbial cell contained in the aqueous acrylamide solution can also be calculated using a standard curve made based on the correlation between the turbidity of the aqueous solution (e.g., turbidity at a wavelength of 630 nm) and the dried cell weight concentration obtained using the method described above.

When polymerizing an aqueous acrylamide solution stabilized according to the method of the present invention, depending on the application of a polymerized product, a microbial cell may be separated from the aqueous acrylamide solution before performing polymerization. As long as the performance of the obtained polymerized product is not affected, polymerization may be performed with the microbial cell contained. Further, polymerization may be performed in a state where polysaccharides produced by the microbial cell are contained in the aqueous acrylamide solution. A polymerized product having a higher viscosity can be obtained thereby (International Publication WO 03/080680 pamphlet).

As the method for separating the microbial cell, a conventionally known method can be used. Examples thereof include filtration using a filter (Japanese Publication for Opposition No. H05-49273), filtration using a hollow fiber membrane (International Publication WO 04/089518 pamphlet), and a method utilizing a centrifugal machine (Japanese National-phase PCT Laid-Open Patent Publication No. 2004-528037).

According to the stabilization method of the present invention described above, by adding the microbial cell as a stabilizer, the aqueous acrylamide solution can be stabilized. In addition, the microbial cell used can be easily separated and removed.

It is thought that stabilization by the microbial cell is caused because the microbial cell and a component derived therefrom contained in the aqueous acrylamide solution capture and/or extinguish radicals to suppress polymerization of acrylamide. Further, it is thought that, however, when a large amount of the microbial cell is contained, it reversely becomes the starting point of polymerization to promote polymerization.

International Publication WO 05/054488 pamphlet shows that, in the production of an aqueous acrylamide solution using a microbial cell, when polymerization is performed in the presence of a microbial cell used in a specific formulation, there is no difference between properties (e.g., molecular weight and viscosity) of the polymerized product of acrylamide and those of a polymerized product obtained from an aqueous acrylamide solution not containing any microbial cell. However, almost no examination has been made with respect to influence of microbial cells on the performance of an aqueous acrylamide solution.

In the method of the present invention, an aqueous acrylamide solution is stabilized using a microbial cell as a stabilizer, which can be easily separated unlike conventional stabilizers. Therefore, the method can be suitably used for preventing polymerization of an aqueous acrylamide solution at the time of production, preservation and transportation. In addition, production processes that can be conveniently and stably operated can be constructed when employing the method of the present invention using the microbial cell since no particular stabilizer or apparatus is used in the invention.

Moreover, the method of the present invention is useful for an aqueous acrylamide solution obtained without using a microbial cell, such as a commercially-available acrylamide, because it is easy to carry out separation and removal before obtaining a polymer and the method can be used as a convenient stabilization method.

EXAMPLES

Hereinafter, the present invention will be described in more detail based on working examples and comparative examples, but the present invention is not limited thereto.

Example 1

(1) Preparation of Microbial Cell Having Nitrile Hydratase Activity

*Rhodococcus rhodochrous* J-1 having nitrile hydratase activity (Accession number: FERM BP-1478) (Japanese Publication for Opposition No. H06-55148) was aerobically cultured in a medium (pH 7.0) containing 2% by mass of glucose, 1% by mass of urea, 0.5% by mass of peptone, 0.3% by mass of yeast extract and 0.05% by mass of cobalt chloride at 30° C. for 60 hours in a 30 L Jar fermentor (KK Takasugiseisakusho). 20 L of the obtained culture solution was subjected to cycle filtration through a cross-flow-type hollow fiber membrane module, and 0.1% by mass of aqueous solution of sodium acrylate (pH 7.0) in an amount corresponding to the amount of the filtrate was continuously fed to the culture solution to carry out washing, thereby providing a microbial cell having nitrile hydratase activity.

(2) Production of Acrylamide 32 kg of 0.2 g/L aqueous solution of sodium acrylate was put into a reaction tank having an inner volume of 75 L, and 50 g of the microbial cell having nitrile hydratase activity prepared in item (1) above was added thereto. The obtained mixture was stirred with pH and temperature being controlled to be 7.0 and 15° C., respectively. To this, acrylonitrile was continuously fed so that the concentration thereof was kept at 2% by mass, and a reaction was conducted until the concentration of acrylamide became 47.3% by mass. After that, feed of acrylonitrile was terminated, temperature was set to 20° C., and the reaction was continued until no acrylonitrile was detected in the reaction solution.

(3) Acceleration Test of Polymerization Stability

The aqueous acrylamide solution prepared in item (2) above and 0.1% aqueous solution of sodium acrylate (pH 7.0) were added to a glass container with a lid having an inner volume of 13.5 mL (AS ONE Corporation, No. 9-852-06) to prepare 5 mL of aqueous acrylamide solution (40% by mass) having the dried cell weight concentration of $3.1 \times 10^3$ mg/L. The glass container with the lid was put into a polypropylene container with a lid having an inner volume of 120 mL (TGK, No. 0561-22-54-01), this was left in a hot-air constant-temperature apparatus with temperature being set at 80° C., and time required for 40% by mass of aqueous acrylamide solution to be polymerized to provide a popcorn-like form was measured.

Examples 2-3

In the acceleration test of polymerization stability in Example 1 (3), time required for polymerization was measured in a manner similar to that in Example 1, except that the microbial cell having nitrile hydratase activity prepared in Example 1 (1) and 0.1% aqueous solution of sodium acrylate (pH 7.0) were added to the aqueous acrylamide solution prepared in Example 1 (2) and that the dried cell weight concentration of the microbial cell contained in 40% by mass of aqueous acrylamide solution (5 mL) was changed as shown in Table 1.

Examples 4-7

After the production of acrylamide in Example 1 (2), the reaction solution after the termination of the reaction was subjected to filtration using a filter having a pore diameter of 0.45 μm (ADVANTEC, No. A045A047A) to remove the microbial cell, thereby preparing 50% by mass of aqueous acrylamide solution not containing the microbial cell (corresponding to "purified solution" in Table 1). Time required for polymerization was measured in a manner similar to that in Example 1, except that the microbial cell having nitrile hydratase activity prepared in Example 1 (1) and 0.1% aqueous solution of sodium acrylate (pH 7.0) were added to 50% by mass of the aqueous acrylamide solution and that the dried cell weight concentration of the microbial cell contained in 40% by mass of aqueous acrylamide solution (5 mL) was changed as shown in Table 1.

Comparative Example 1

Time required for polymerization was measured in a manner similar to that in Example 1, except that 40% by mass of aqueous acrylamide solution not containing the microbial cell (5 mL) was prepared using 50% by mass of the aqueous acrylamide solution not containing the microbial cell prepared in Examples 4-7 and 0.1% by mass of aqueous solution of sodium acrylate (pH 7.0).

Comparative Example 2

Time required for polymerization was measured in a manner similar to that in Example 1, except that in Examples 4-7, the dried cell weight concentration of the microbial cell contained in 40% by mass of aqueous acrylamide solution (5 mL) was changed as shown in Table 1.

The results of Examples 1-7 and Comparative Examples 1-2 described above are shown in Table 1 below and FIG. 1.

TABLE 1

| | Strain | Dried cell weight concentration [mg/L] | Time required for polymerization [day] | Remarks |
|---|---|---|---|---|
| Example 2 | J-1 | $1.4 \times 10^4$ | 28 | Reaction solution + microbial solution |
| Example 3 | J-1 | $6.2 \times 10^3$ | 42 | Reaction solution + microbial solution |
| Example 1 | J-1 | $3.1 \times 10^3$ | 42 | Reaction solution |
| Example 4 | J-1 | $1.4 \times 10^3$ | 41 | Purified solution + microbial solution |
| Example 5 | J-1 | $6.2 \times 10^2$ | 37 | Purified solution + microbial solution |

TABLE 1-continued

| Strain | Dried cell weight concentration [mg/L] | Time required for polymerization [day] | Remarks |
|---|---|---|---|
| Example 6 | J-1 | $3.1 \times 10^2$ | 25 | Purified solution + microbial solution |
| Example 7 | J-1 | 90 | 22 | Purified solution + microbial solution |
| Comparative Example 1 | None | 0 | 14 | Purified solution |
| Comparative Example 2 | J-1 | $2.8 \times 10^4$ | 1 | Purified solution + microbial solution |

As shown in Table 1, in Examples 1-7 using the stabilization method of the present invention, time required for polymerization of acrylamide is long, and it was observed that the obtained aqueous acrylamide solution was highly-effectively stabilized. Further, when Examples 1-7 are compared to each other, to the extent that the dried cell weight concentration of the microbial cell was about 6500 mg/L, the more the content of the microbial cell was, the more difficult the polymerization of acrylamide was. Particularly high stabilization effect was shown even when compared to the case where the content was more that that.

Meanwhile in Comparative Example 2 in which the content of the microbial cell in the aqueous acrylamide solution was too much, time required for polymerization of acrylamide was very short, and the stability was lower.

Further, in Comparative Example 1 in which the microbial cell was not contained in the aqueous acrylamide solution, time required for polymerization of acrylamide was shorter compared to the Examples and the stability was lower.

Example 8

<Working Example Using a *Rhodococcus* Bacterium and a Commercially-Available Acrylamide>
(1) Preparation of Microbial Cell Having Nitrile Hydratase Activity As the microbial cell having nitrile hydratase activity, *Rhodococcus rhodochrous* J-1 (Accession number: FERM BP-1478) (Japanese Publication for Opposition No. H06-55148) was used. To a 500 mL conical flask, 100 mL of a medium having the aforementioned composition was added, and sterilization was performed using an autoclave at 121° C. for 20 minutes. A cryopreserved cell was seeded in this medium and culturing was performed at 30° C. at 130 rpm for 75 hours.

A culture solution obtained by the aforementioned culturing was subjected to centrifugation (15000 G×10 minutes) to separate only the cell from the culture solution. Subsequently, the cell was resuspended in 50 mL of water, and after that, centrifugation was performed again to obtain a wet cell. The wet cell was washed with water three times, thereby providing a microbial cell having nitrile hydratase activity.
(2) Acceleration Test of Polymerization Stability To a glass container with a lid having an inner volume of 13.5 mL (AS ONE Corporation, No. 9-852-06), the microbial cell having nitrile hydratase activity prepared in (1) above, water and a commercially-available acrylamide (Wako Pure Chemical Industries, Ltd., No. 019-10025) were added to prepare 45% by mass of aqueous acrylamide solution (5 mL) having a dried cell weight concentration of 20 mg/L. The glass container with the lid was put into a polypropylene container with a lid having an inner volume of 120 mL (TGK, No. 0561-22-54-01), and this was left in a hot-air constant-temperature apparatus with temperature being set at 50° C. for 21 days. After that, temperature was set at 80° C., and then time required for 45% by mass of the aqueous acrylamide solution to be polymerized to provide a popcorn-like form was measured.

Examples 9 and 10

Time required for polymerization was measured in a manner similar to that in Example 8, except that in the acceleration test of polymerization stability in Example 8 (2), the dried cell weight concentration of the microbial cell contained in 45% by mass of the aqueous acrylamide solution (5 mL) was changed as shown in Table 2.

Examples 11-13

Time required for polymerization was measured in a manner similar to that in Example 8, except that in the preparation of the microbial cell having nitrile hydratase activity in Example 8 (1), the microbial cell to be used was changed to *Rhodococcus rhodochrous* M8 (VKPMB-S926) and that the dried cell weight concentration of the microbial cell contained in 45% by mass of aqueous acrylamide solution (5 mL) was changed as shown in Table 2.

Comparative Example 3

Time required for polymerization was measured in a manner similar to that in Example 8, except that 45% by mass of aqueous acrylamide solution (5 mL) not containing the microbial cell was prepared using water and a commercially-available acrylamide.

The results of Examples 8-13 and Comparative Example 3 described above are shown in Table 2 below.

TABLE 2

| | Strain | Dried cell weight concentration [mg/L] | Time required for polymerization [day] (*) |
|---|---|---|---|
| Example 8 | J-1 | 10 | 7 |
| Example 9 | J-1 | 20 | 8 |
| Example 10 | J-1 | 50 | 10 |
| Example 11 | M8 | 10 | 8 |
| Example 12 | M8 | 20 | 15 |
| Example 13 | M8 | 50 | 15 |
| Comparative Example 3 | None | 0 | 1 |

(*) Number of days since temperature was changed to 80° C. after preserved at 50° C. for 21 days.

As shown in Table 2, in Examples 8-13 using the stabilization method of the present invention, time required for polymerization of acrylamide was long, and it was observed that the obtained aqueous acrylamide solution was highly-effectively stabilized.

Meanwhile in Comparative Example 3 in which the microbial cell was not contained in the aqueous acrylamide solution, time required for polymerization of acrylamide was shorter compared to the Examples, and the stability was lower.

Example 14

<Working Example Using *E. coli* and a Commercially-Available Acrylamide>
(1) Preparation of Microbial Cell As the microbial cell having nitrile hydratase activity, *Escherichia coli* MT-10822 (Accession number: FERM BP-5785) (Japanese Laid-Open Patent Publication No. H09-275978) was used. 100 mL of a medium having the aforementioned composition was added to a 500 mL conical flask, and it was subjected to sterilization using an autoclave at 121° C. for 20 minutes. A cryopreserved cell was seeded in this medium and culturing was performed at 37° C. at 130 rpm for 20 hours.

A culture solution obtained by the aforementioned culturing was subjected to centrifugation (15000 G×10 minutes) to separate only the cell from the culture solution. Subsequently, the cell was resuspended in 50 mL of water, and after that, centrifugation was performed again to obtain a wet cell. The wet cell was washed with water three times, thereby providing a microbial cell having nitrile hydratase activity.

(2) Acceleration Test of Polymerization Stability

To a glass container with a lid having an inner volume of 13.5 mL (AS ONE Corporation, No. 9-852-06), the microbial cell having nitrile hydratase activity prepared in (1) above, water and a commercially-available acrylamide (Wako Pure Chemical Industries, Ltd., No. 019-10025) were added to prepare 44% by mass of aqueous acrylamide solution (5 mL) having a dried cell weight concentration of 24 mg/L. The glass container with the lid was put into a polypropylene container with a lid having an inner volume of 120 mL (TGK, No. 0561-22-54-01), and this was left in a hot-air constant-temperature apparatus with temperature being set at 70° C. Then, time required for 44% by mass of the aqueous acrylamide solution to be polymerized to provide a popcorn-like form was measured.

Examples 15-16

Time required for polymerization was measured in a manner similar to that in Example 14, except that in the acceleration test of polymerization stability in Example 14 (2), the dried cell weight concentration of the microbial cell contained in 44% by mass of aqueous acrylamide solution (5 mL) was changed as shown in Table 3.

Comparative Example 4

Time required for polymerization was measured in a manner similar to that in Example 14, except that 44% by mass of aqueous acrylamide solution (5 mL) not containing the microbial cell was prepared using water and a commercially available acrylamide.

Comparative Example 5

Time required for polymerization was measured in a manner similar to that in Example 14, except that in the acceleration test of polymerization stability in Example 14 (2), the dried cell weight concentration of the microbial cell contained in 44% by mass of aqueous acrylamide solution (5 mL) was changed as shown in Table 3.

The results of Examples 14-16 and Comparative Examples 4-5 described above are shown in Table 3 below.

TABLE 3

| Strain | Dried cell weight concentration [mg/L] | Time required for polymerization [day] |
| --- | --- | --- |
| Example 14 | MT-10822 | 10 | 27 |
| Example 15 | MT-10822 | 25 | 33 |
| Example 16 | MT-10822 | 130 | 33 |
| Comparative Example 4 | None | 0 | 19 |
| Comparative Example 5 | MT-10822 | $2.0 \times 10^4$ | 1 |

As shown in Table 3, in Examples 14-16 using the stabilization method of the present invention, time required for polymerization of acrylamide is long, and it was observed that the obtained aqueous acrylamide solution was highly-effectively stabilized.

Meanwhile in Comparative Example 5 in which the content of the microbial cell in the aqueous acrylamide solution was too much, time required for polymerization of acrylamide was very short, and the stability was lower.

Further, in Comparative Example 4 in which the microbial cell was not contained in the aqueous acrylamide solution, time required for polymerization of acrylamide was shorter compared to the Examples and the stability was lower.

INDUSTRIAL APPLICABILITY

According to the stabilization method of the present invention, an aqueous acrylamide solution can be conveniently stabilized, and a microbial cell used as a stabilizer can be easily separated and removed. Therefore, the method can be suitably used as a method for preventing polymerization of an aqueous acrylamide solution at the time of production, preservation and transportation.

The invention claimed is:

1. A method for preventing polymerization of an aqueous acrylamide solution during preservation and/or transportation of the acrylamide solution comprising:
    adding a microbial cell having nitrile hydratase activity to the aqueous acrylamide solution at a dried cell weight concentration of 1 to 14000 mg/L, wherein the microbial cell having nitrile hydratase activity is selected from the group consisting of *Rhodococcus rhodochrous*, *Escherichia coli* MT-10822 (Accession number: FERM BP-5785), and mixtures thereof, and
    preserving and/or transporting the acrylamide solution in the presence of the microbial cell,
    wherein the presence of the microbial cell in the acrylamide solution prevents polymerization of the aqueous acrylamide solution.

2. The method according to claim 1, wherein the dried cell weight concentration is 10 to 14000 mg/L.

3. The method according to claim 1, wherein the *Rhodococcus rhodochrous* is selected from the group consisting of *Rhodococcus rhodochrous*J-1 (Accession number: FERM BP-1478), *Rhodococcus rhodochrous* M8 (Accession number: VKPMB-S926), and mixtures thereof.

4. The method according to claim 1 wherein the microbial cell is added at the time of preparation of the aqueous acrylamide solution from an aqueous acrylonitrile solution.

5. The method according to claim 1, wherein the nitrile hydratase activity is an activity which produces an acrylamide from an acrylonitrile.

6. The method according to claim 1, wherein the acrylamide has been produced from an acrylonitrile using the microbial cell having nitrile hydratase activity.

7. The method of claim 1, wherein the microbial cell is added after preparation of the aqueous acrylamide solution.

8. A method for reducing foamability of an acrylamide solution during transportation, concentration, distillation, and/or crystallization of the acrylamide solution comprising:
    adding a microbial cell having nitrile hydratase activity to the aqueous acrylamide solution at a dried cell weight concentration of 500 mg/L or lower, and
    transporting, concentrating, distilling, and/or crystallizing the acrylamide solution in the presence of the microbial cell, wherein the microbial cell having nitrile hydratase activity is selected from the group consisting of *Rhodococcus rhodochrous, Escherichia coil* MT-10822 (Accession number: FERM BP-5785), and mixtures thereof, and wherein the presence of the microbial cell in the acrylamide solution reduces foamability of the aqueous acrylamide solution.

* * * * *